United States Patent [19]

Jore

[11] Patent Number: 5,320,606
[45] Date of Patent: Jun. 14, 1994

[54] SINGLE USE HYPODERMIC SAFETY SYRINGE

[76] Inventor: Matthew B. Jore, P.O. Box 735, Ronan, Mont. 59864

[21] Appl. No.: 32,494

[22] Filed: Mar. 17, 1993

[51] Int. Cl.⁵ .............................................. A61M 5/00
[52] U.S. Cl. ..................................... 604/110; 604/195; 604/198
[58] Field of Search ............... 604/110, 187, 192, 195, 604/197, 198, 218, 231; 128/919

[56] References Cited

U.S. PATENT DOCUMENTS

| | | | |
|---|---|---|---|
| 4,741,737 | 5/1988 | Meyer et al. | 604/140 |
| 4,874,382 | 10/1989 | Lindemann et al. | 604/195 |
| 4,936,830 | 6/1990 | Verlier | 604/110 |
| 4,973,316 | 11/1990 | Dysarz | 604/195 |
| 5,092,853 | 3/1992 | Couvertier | 604/195 |
| 5,176,656 | 1/1993 | Bayless | 604/198 |
| 5,190,526 | 3/1993 | Murray et al. | 604/110 |
| 5,209,739 | 5/1993 | Talalay | 604/195 |

Primary Examiner—C. Fred Rosenbaum
Assistant Examiner—Vanitha Alexander
Attorney, Agent, or Firm—Richard C. Conover

[57] ABSTRACT

The present invention relates to a disposable medical syringe which has a hollow plunger to receive a used inoculation needle. The syringe has a hollow syringe barrel, open on one end and closed on the other. A hollow plunger assembly, which extends out the open end of the syringe barrel, has a hollow tube with a fixed seal attached at one end. At the other end of the plunger assembly, a needle holder is sized to slide within the hollow tube. The sliding seal and needle holder are biased toward each other by a stretched, resilient tube that has a fluid passageway passing through the sliding seal, resilient tube, and needle holder. The needle holder is normally locked at one end of the plunger assembly by a locking means. As the syringe is collapsed, the syringe barrel trips the locking means to permit the needle holder, and attached inoculation needle, to be retracted into the hollow tube. The three components—inoculation needle, hollow tube, and syringe barrel—are telescoped together by this action to compact the throw-away unit with the used inoculation needle resting in a position protected by the double outer walls.

5 Claims, 2 Drawing Sheets

SINGLE USE HYPODERMIC SAFETY SYRINGE

BACKGROUND OF THE INVENTION

This invention relates to an improved single use hypodermic safety syringe, and more specifically to a plunger within the syringe which permits a conventional inoculation needle to be retracted to a position within the plunger.

Hypodermic syringes are well known in the art having been used for many years in the medical profession. In recent years the problem of a person using a syringe and becoming infected by an inadvertent prick from a used inoculation needle has intensified the search for a hypodermic syringe which protects those who might have to handle it.

Several devices have used a spring-loaded cover to shield an inoculation needle after it has been withdrawn from a person receiving an inoculation. For instance see U.S. Pat. No. 4,900,311 to Stern et at., U.S. Pat. No. 4,955,868 to Klein, or U.S. Pat. No. 4,966,592 to Burns et al. In each of these devices, the shield becomes rather unwieldy because it has to have a rather large cross-section so as so slide around the syringe barrel. The large cross-section prevents the person using the hypodermic syringe from accurately locating an insertion point because the insertion point is covered by the shield. Also since the inoculation needle is capped after the needle is used, an elongated shape is maintained. The elongated shape makes it easier to snap off both the guard and inoculation needle if the syringe barrel is inadvertently held for some reason and someone hits the syringe.

Several other devices have inoculation needles moving through a protective guard which is smaller than the syringe barrel near the insertion tip of an inoculation needle. For instance see U.S. Pat. No. 2,925,083 to Craig, U.S. Pat. No. 4,911,693 to Paris, or U.S. Pat. No. 5,135,510 to Maszkiewicz et al. The insertion point can be seen easier with the latter mentioned devices since the guard is of much smaller diameter, but the inoculation needle still remains at the end of an elongated device. It is much easier to snap an elongated device when it gets inadvertently held near one end. The leverage is such that there are times when an inoculation needle could be exposed just because the syringe barrel got caught in some unusual manner.

None of the above inventions have recognized the fact that an inoculation needle can be drawn back into the syringe barrel to compact the unit that is thrown away. Other inventions illustrate devices which use a spring to retract an inoculation needle inside a plunger. For instance see U.S. Pat. No. 4,994,034 to Botich et al., U.S. Pat. No. 5,017,187 to Sullivan, or U.S. Pat. No. 5,019,044 to Tsao. These devices, however, can not accept conventional inoculation needles as the needles used in these devices are either spring loaded during assembly, or are specially configured for the device to function properly. In addition, all off these devices have a plunger entering from the rear of a syringe barrel in a manner similar to that used in a conventional syringe. This means there has to be some type of sliding surface between the syringe barrel and the plunger which is open to the atmosphere. This sliding surface is a possible source of contamination.

Thus there appears to be a need for a syringe which can hold inoculation fluid in a volume which does not have sealing surfaces exposed to the atmosphere. This would reduce the possibility of possible contamination as the plunger is pulled out and pushed in. In addition a need exists to have a syringe which uses conventional needles which can be retracted into both the plunger and, the syringe barrel. This would simplify the devices used use in current medical facilities. A need also exists to have a double surface surrounding a used needle to provide additional protection against exposure as compared with those instances where only a single surface of a syringe barrel is used. And lastly, a device should be compacted in its disposal state so as to reduce the possibility of inadvertent breakage of an elongated object when the device is caught in some unusual manner.

SUMMARY OF INVENTION

The present invention relates to a single use hypodermic safety syringe which has a hollow plunger to receive a used inoculation needle.

The syringe has a hollow syringe barrel, open on one end and closed on the other, which can hold inoculating fluid adjacent the closed end when the syringe is being used. A hollow plunger assembly is inserted into the open end of the syringe barrel to exert pressure on the inoculating fluid when the syringe barrel and plunger are pressed together.

The hollow plunger assembly, which extends out the end of the syringe barrel closest to an inoculating needle, has a hollow tube with a fixed seal attached at one end that can slide along and within the syringe barrel. At the other end of the plunger assembly, a needle holder, which holds the inoculation needle, is sized to slide within the hollow tube. The sliding seal and needle holder are biased toward each other by a stretched, resilient tube that is attached to both the sliding seal and the needle holder. A fluid passageway passes through the sliding seal, resilient tube, and needle holder to allow inoculating fluid to flow from the closed end of the syringe barrel through the needle holder and attached needle whenever the syringe barrel and plunger assembly are pressed together.

The needle holder is normally locked at one end of the plunger assembly by a locking means. Once the syringe is to be used, a conventional inoculation needle is connected to the needle holder. As the syringe is collapsed, the syringe barrel trips the locking means at the completion of the inoculation stroke. This permits the needle holder, and attached inoculation needle, to be retracted into the hollow tube by the action of the resilient tube biasing the needle holder toward the sliding seal. The length of the hypodermic syringe is significantly reduced when the used inoculation needle is pulled into the retracted position since the syringe barrel covers, and the inoculation needle is withdrawn into, the plunger assembly. In this position the inoculation needle rests in the interior of a compact throw-away unit where both the hollow tube wall and the syringe barrel wall protect it from inadvertent exposure. The three components—inoculation needle, hollow tube, and syringe barrel—are telescoped together to compact the throw-away unit.

BRIEF DESCRIPTION OF THE DRAWINGS

In order that the invention may be clearly understood and readily carried into effect, a preferred embodiment of the invention will now be described, by way of example only, with reference to the accompanying drawings wherein.

DESCRIPTION OF A PREFERRED EMBODIMENT

Figure 1:
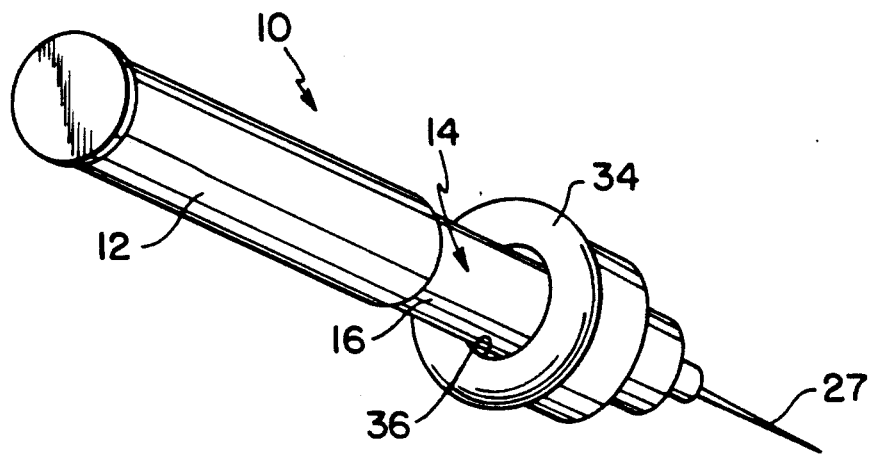
FIG. 1 is perspective view of the present invention.
Figure 2:
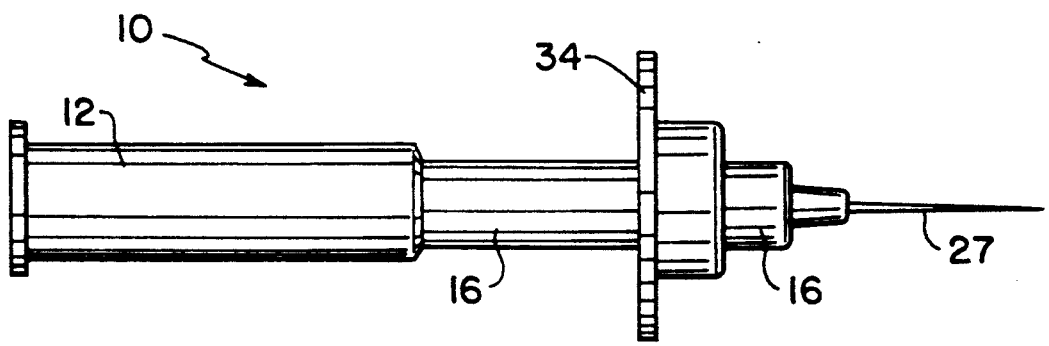
FIG. 2 is an elevational view of the invention shown in FIG. 1.

A preferred embodiment of the single use hypodermic safety syringe 10 is shown in FIG. 1. Single use hypodermic safety syringe 10 has a hollow syringe barrel 12 which is closed at one end and open at the other end. A plunger assembly 14 sealingly slides in the interior of syringe barrel 12 so as to place pressure on any inoculating fluid that is in syringe barrel volume 15. Volume 15 is completely enclosed by the closed end of syringe barrel 12 and plunger assembly 14 thus isolating volume 15 from the atmosphere and any possible contamination. Plunger assembly 14 has a hollow tube 16 that is open at both ends. Sliding seal 18 is attached to an end of hollow tube 16 in a manner such that the sliding seal cannot be dislodged, or pulled into the hollow tube. Sliding seal 18 is also sized to sealing slide along the interior wall of syringe barrel 12 to prevent inoculation fluid from escaping around the seal. The thickness of sliding seal 18 is also such that it engages the closed end of syringe barrel 12 before the syringe barrel can complete an inoculation stroke. A hollow post 20, formed as a part of sliding seal 18, extends into hollow tube 16. Fluid passageway 22 also extends through sliding seal 18 and hollow post 20 into volume 21 of hollow tube 16 so as to provide a fluid passageway completely through the seal.

At the other end of hollow tube 16, a needle holder 24 is sized to slide freely along an interior surface of the hollow tube. Needle holder 24 on one side has a hollow screw post 26 to receive an inoculation needle 27, and on the opposite side has a hollow post 28. Hollow screw post 26 is threaded in the preferred embodiment to receive a conventional inoculation needle having a conventional LUER LOCK threaded connection, although a frictional mating surface could as easily be used with alternative inoculation needles. Fluid passageway 30 extends completely through inoculation needle holder 24 to permit inoculating fluid to flow through the needle holder and on through the hollow inoculation needle.

A resilient tube 32 is attached on one end to hollow post 20 and on the opposite end to hollow post 28 to provide a fluid passageway between the two hollow posts through the resilient tube. In the preferred embodiment, resilient tube 32 also provides a biasing means to pull needle holder 24 toward sliding seal 18 whenever the needle holder is unlocked. It should be recognized, however, that a spring connected in tension between sliding seal 18 and needle holder 24, or a spring placed in compression between a position adjacent the open end of syringe barrel 12 and needle holder 24 could be used equally as effectively to provide the same type of bias.

Figure 3:
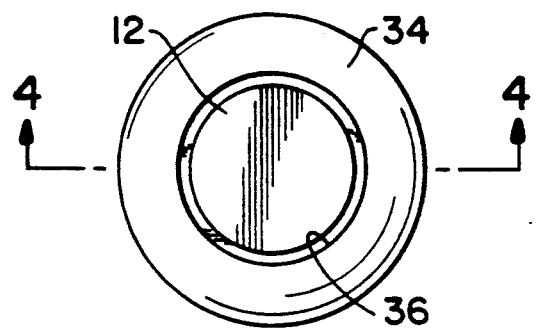
FIG. 3 is an end view of the invention shown in FIG. 2.
Figure 4:
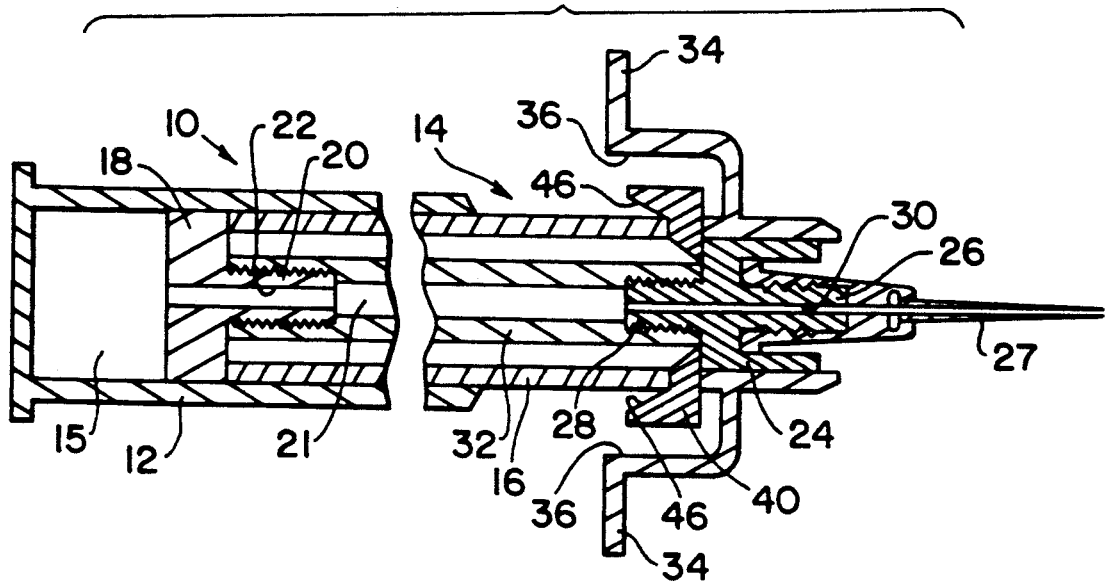
FIG. 4 is a sectional view of the invention taken along the line 4—4 shown in FIG. 3.
Figure 5:
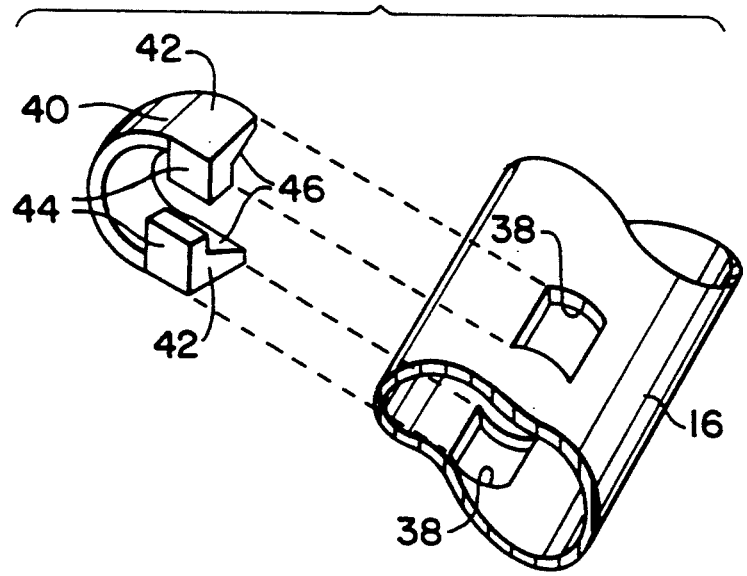
FIG. 5 is a perspective view with parts broken away of two elements shown in FIG. 4.

Hollow tube 16 also has a finger rest 34, which in FIGS. 1 and 3 is shown as a ring but which could just as easily be a pair of finger retaining flanges, fixedly connected to the hollow tube and extending away from the exterior surface. As best seen in FIG. 4, finger rest 34 is spaced apart from hollow tube 15 by an opening 36 on a side nearest syringe barrel 12 to permit the syringe barrel to move into the opening as the inoculating stroke nears completion. As best seen in FIG. 5, hollow tube 16 also has a pair of tab openings 38 on each side of the hollow tube to receive cooperating tabs. A tab locking ring 40 has tabs 42 at either end which tabs are sized to easily fit within tab openings 38. As best seen in FIG. 5, tabs 42 are shaped so as to have a flat locking surface 44 to slide across and hold needle holder 24 at one end of hollow tube 16, and also have a cammed release surface 46 which be cammed outward by syringe barrel 12. As syringe barrel 12 moves against cammed release surface 46, the cammed release surface is cammed outward to remove flat locking surface 44 from the locking position over needle holder 24. Needle holder 24 is then free to move toward sliding seal 18 under the biasing action of resilient tube 32. This movement withdraws inoculation needle 27 into the interior of hollow tube 16.

To prevent the premature engaging of the tab locking ring 40 by syringe barrel 12, sliding seal 18 has sufficient thickness to engage the closed end of syringe barrel 12 before the syringe barrel can engage cammed release surface 46. Sliding seal 18 then has to be compressed to allow the final push of the syringe barrel toward and into cammed release surface 46. This reduces the possibility of syringe barrel 12 prematurely engaging the cammed release surface 46 when filling the syringe with inoculation fluid.

In operation needle holder 24 is pulled away from sliding seal 18 and locked into position as flat locking surface, 44 on tab 42 slides across the needle holder. A conventional inoculation needle 27 is screwed onto the LUER LOCK attachment on hollow screw post 26 on needle holder 24 when the device is to be used so that the injection syringe can be used in a conventional manner. Single use hypodermic safety syringe 10 is then inserted into a bottle of inoculating fluid and syringe barrel 12 pulled away from the inoculation needle. This action pulls inoculating fluid into the enclosed and isolated syringe barrel volume 15 through the fluid passageway extending from outside inoculation needle 27 through sliding seal 18.

When inoculating with single use hypodermic safety syringe 10, a person places his fingers on finger rest 34 and thumb on the closed end of syringe barrel 12 and squeezes the inoculating fluid out of the syringe. As the inoculating stroke nears completion, syringe barrel 12 enters opening 36. Syringe barrel 12 then contacts cammed release surface 46 and spreads tabs 42 outward from hollow tube 16 to release the lock on needle holder 24. When flat locking surface 44 is cammed to a position outside needle holder 24 and within the walls of hollow tube 16, the needle holder is free to slide. Needle holder 24 with attached inoculation needle 27 is then pulled toward sliding seal 18 by the biasing action of resilient tube 32. This positions inoculation needle 27 inside both hollow tube 16 and syringe barrel 12. In this protected position, inoculation needle 27 is surrounded by both the hollow tube 16 and syringe barrel 12 walls. The single use hypodermic safety syringe has also been placed in its compacted configuration; syringe barrel 12 surrounds hollow tube 16, and the hollow tube surrounds the inoculation 27 located in the center. Single use hypodermic safety syringe 10 in this compacted position is ready for discarding.

While the fundamental novel features of the invention have been shown and described, it should be understood that various substitutions, modifications and variations may be made by those skilled in the art without departing from the spirit or scope of the invention. Accordingly, all such modifications or variations are included in the scope of the invention as defined by the following claims.

I claim:

1. A syringe for inoculating fluids through an inoculation needle, the syringe comprising:
   a syringe barrel having an inside surface and a closed end and an open end;
   a hollow tube, sized to slide within the syringe barrel, the hollow tube having a first end positioned within the syringe barrel and a second end;
   a sliding seal fixed adjacent the first end and providing a sliding seal between the hollow tube and the inside surface, the sliding seal further having a fluid passageway therethrough connecting a volume within the syringe barrel to a volume within the hollow tube;
   a resilient tube, attached at one end to the sliding seal in fluid communication with the fluid passageway, the tube extending toward the second end;
   a needle holder, attached on the opposite end of the resilient tube, the needle holder sized to slide freely within the hollow tube;
   the needle holder also having the inoculation needle attached and further having a fluid passageway extending from the resilient tube through the needle holder and on through the inoculation needle;
   a biasing means for biasing the needle holder toward the first end;
   a locking means, anchored by the hollow tube, for locking the needle holder adjacent the second end and releasing the needle holder to retract the inoculation needle within the hollow tube whenever the syringe barrel moves adjacent the second end.

2. A syringe according to claim 1 further including:
   a finger rest attached to the hollow tube.

3. A syringe according to claim 1 wherein the needle holder LUER LOCk threads on one end.

4. A syringe according to claim 1 wherein the hollow tube has a tab opening adjacent the second end; and
   the locking means is a tab locking ring having a locking surface biased to protrude through the tab opening and extend into the hollow tube, the tab further having a cammed release surface for camming the tab away from the hollow tube whenever the syringe barrel cams against the cammed release surface.

5. A syringe according to claim 1 wherein the biasing means is the resilient tube stretched between the sliding seal and the needle holder.

* * * * *